US010365200B2

(12) United States Patent
Liu et al.

(10) Patent No.: US 10,365,200 B2
(45) Date of Patent: Jul. 30, 2019

(54) METHOD FOR DETERMINING UNCONVENTIONAL LIQUID IMBIBITION IN LOW-PERMEABILITY MATERIALS

(71) Applicant: Aramco Services Company, Houston, TX (US)

(72) Inventors: Hui-Hai Liu, Katy, TX (US); Bitao Lai, Katy, TX (US); JinHong Chen, Katy, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 284 days.

(21) Appl. No.: 15/160,858

(22) Filed: May 20, 2016

(65) Prior Publication Data
US 2016/0341652 A1 Nov. 24, 2016

Related U.S. Application Data

(60) Provisional application No. 62/165,406, filed on May 22, 2015.

(51) Int. Cl.
*G01N 15/08* (2006.01)
*G01N 33/24* (2006.01)

(52) U.S. Cl.
CPC ............. *G01N 15/08* (2013.01); *G01N 33/24* (2013.01); *G01N 2015/0813* (2013.01); *G01N 2015/0866* (2013.01)

(58) Field of Classification Search
CPC .............. G01N 15/08; G01N 33/24; G01N 2015/0813; G01N 2015/0866; G01N 15/88
See application file for complete search history.

(56) References Cited

U.S. PATENT DOCUMENTS

| | | | | |
|---|---|---|---|---|
| 4,398,416 A | * | 8/1983 | Nolte | E21B 43/26 166/250.1 |
| 5,005,643 A | * | 4/1991 | Soliman | E21B 43/26 166/250.1 |
| 8,195,399 B2 | | 6/2012 | Gladkikh et al. | |
| 8,805,616 B2 | | 8/2014 | Hinkel et al. | |
| 2004/0020642 A1 | * | 2/2004 | Vinegar | B09C 1/02 166/245 |
| 2006/0015310 A1 | | 1/2006 | Husen et al. | |

(Continued)

FOREIGN PATENT DOCUMENTS

WO 2015020735 A1 2/2015

OTHER PUBLICATIONS

Ouyang, "Theoretical and Numerical Simulation of Non-Newtonian Fluid Flow in Propped Fractures," Texas A&M University, 2013.*

(Continued)

*Primary Examiner* — Mohamed Charioui
*Assistant Examiner* — Catherine T. Rastovski
(74) *Attorney, Agent, or Firm* — Bracewell LLP; Constance G. Rhebergen; Kevin R. Tamm

(57) ABSTRACT

The disclosure relates to methods for determining imbibition of hydraulic fracturing fluids into hydrocarbon-bearing formations. More specifically, the disclosure relates to laboratory methods for determining certain unconventional flow parameters to measure the imbibition over time of hydraulic fracturing fluids into a low-permeability hydrocarbon-bearing rock formation.

10 Claims, 9 Drawing Sheets

(56) References Cited

U.S. PATENT DOCUMENTS

| | | | | |
|---|---|---|---|---|
| 2009/0200016 A1* | 8/2009 | Goodwin | ........ | E21B 47/10 166/248 |
| 2011/0061860 A1* | 3/2011 | Dean | ........ | E21B 43/00 166/250.01 |
| 2011/0184711 A1 | 7/2011 | Altman et al. | | |
| 2015/0060058 A1* | 3/2015 | Morris | ........ | E21B 43/26 166/250.02 |
| 2016/0108705 A1* | 4/2016 | Maxwell | ........ | E21B 43/267 166/250.1 |
| 2017/0275970 A1* | 9/2017 | Crawford | ........ | E21B 41/0092 |

OTHER PUBLICATIONS

Sharma et al., "A Treatise on Non-Darcy Flow Correlations in Porous Media," J Pet Environ Biotechnol 2017, 8:5.*

Tan et al., "Analysis of transient flow and starting pressure gradient of power-law fluid in fractal porous media." International Journal of Modern Physics C, 2015.*

Tapscott, "An Evaluation of Flow and Transport Properties for Hydraulic Fracturing Fluids in Porous Medium Systems," University of North Carolina, 2015.*

Hu et al., "Integrated Experimental and Mode3ling Approaches to Studying the Fracture-Matrix Interaction in Gas Recovery from Barnett Shale", RPSEA Final Reports Feb. 28, 2014.*

Liu et al., "Unsaturated properties for non-Darcian water flow in clay", J Hydrology 430-431 (2012).*

Roychaudhuri R., Tsotsis,. T.T. and Jessen, K., 2013. An experimental investigation of spontaneous imbibition in gas shales. Journal of Petroleum Science and Engineering 111: 87-97.

Rangel-German, E.R., Kovscek, A.R., 2002. Experimental and analytical study of multidimensional imbibition in fractured porous media, Journal of Petroleum Science and Engineering 36(1-2): 45-60.

Blecker, R.F., 1970. Saturated flow of water through clay loam subsoil material of the Brolliat and Springerville soil series. Master Thesis, University of Arizona.

Brutsaert W., 1982. Some exact solutions for non-linear desorptive diffusion. Journal of Applied Mathematics and Physics 33: 540-546.

Buckingham, E. 1907. Studies on the movement of soil moisture. Bulletin 38. USDA Bureau of Soils, Washington, DC.

Pagels, M., Willberg, D.M., and Edelman, E., et al., 2013. Quantifying fracturing fluid damage on reservoir rock to optimize production. Paper URTeC 1578948 presented at the Unconventional Resources Technology Conference held in Denver, Colorado, USA, Aug. 12-14, 2011.

Nimmo, J. R., and Landa, E.R., 2005. The soil physics contributions of Edgar Buckingham. Soil. Sci. Am. J. 69:328-342.

Evangelides C., Arampatzis G., and Tzimopoulos C., 2010. Estimation of soil moisture profile and diffusivity using simple laboratory procedures. Soil Science 17 5(3): 118-127.

Miller, R.J., and Low P.F., 1961 Threshold gradient for water flow in clay systems. Soil. Sci. Soc. Am. Proc. 27(6), 605-609.

Hansbo, S., 2001. Consolidation equation valid for both Darcian and non-Darcian flow. Geotechnique 51(1), 51-54.

Hu, Q.H., and R. P. Ewing, 2014. Integrated experimental and modeling approaches to studying the fracture-matrix interaction in gas recovery from Barnett shale. Report 09122-12. University of Texas at Arlington.

Liu, H.H., 2011. A conductivity relationship for steady-state unsaturated flow processes under optimal flow conditions. Vadose Zone Journal 10(2), 736-740.

Liu, H.H. and Birkholzer, J., 2012. On the relationship between water-flux and hydraulic gradient for unsaturated and saturated clay. Journal of Hydrology, 475, 242-247.

Liu, H.H., 2014a. Non-Darcian flow in low-permeability media: Key issues related to geological disposal of high-level nuclear waste in shale formations. Hydrogeology Journal, DOI 10.1007/s10040-014-1145-x.

Liu, H.H., 2014b. A thermodynamic hypothesis regarding optimality principles for flow processes in geosystems. Chinese Science Bulletin, 59( 16) 1880-1884.

Wen, Z., 2014. Non-Darcian flow toward a larger-diameter partially penetrating well in a confined aquifer. Environ Earth Sci (2014) 72:4617-4625.

Wen, Z., 2006. Non-Darcian flow in a single confined vertical fracture toward a well. Journal of Hydrology (2006) 330, 698-708.

McElwee, C.D., 1998. A nonlinear model for analysis of slug-test data. Water Resources Research, vol. 34, No. 1, 55-66.

Qian, J.Z., 2011. Solute transport in a filled single fracture under non-Darcian flow. International Journal of Rock Mechanics & Mining Sciences.

Bordier, C., 1999. Drainage equations and non-Darcian modelling in coarse porous media or geosynthetic materials. Journal of Hydrology, 228 (2000) 174-187.

Swartzendruber, D. 1961. Modification of Darcy's law for the flow of water in soils. Soil Science 93: 22-29. Soil. Sci. Soc. Am. J. 69, 328-342.

Xu, S.L., Yue, X.A., Hou, J.R., 2007. Experimental investigation on flow characteristics of deionized water in microtubes. Chinese Science Bulletin 52(6): 849-854.

Zou, Y., 1996. A non-linear permeability relation depending on the activation energy of pore liquid. Geotechnique 46( 4), 769-774.

Bruce et al., "The Measurement of Soil Moisture Diffusivity", Soil Science Society Proceedings, 1956, pp. 458-462.

International Search Report and Written Opinion for related PCT application PCT/US2016/033484 dated Aug. 19, 2016.

Liu et al., "On the relationship between water flux and hydraulic gradient for unsaturated and saturated clay", Journal of Hydrology, 2012, pp. 242-247, vol. 475, Elsevier.

Liu et al., "Unsaturated properties for non-Darcian water flow in clay", Journal of Hydrology, 2012, pp. 173-178, Elsevier.

Qinhong et al., "Integrated Experimental and Modeling Approaches to Studying the Fracture-Matrix Interaction in Gas Recovery from Barnett Shale", RPSEA, 2014, pp. 1-91.

* cited by examiner

METHOD FOR DETERMINING UNCONVENTIONAL LIQUID IMBIBITION IN LOW-PERMEABILITY MATERIALS

RELATED APPLICATIONS

The present application is a non-provisional application of and claims priority to U.S. Provisional Application No. 62/165,406, filed May 22, 2015, the entire disclosure of which is hereby expressly incorporated herein by reference.

BACKGROUND

1. Field

The present disclosure relates to methods for determining an amount of imbibition of hydraulic fracturing fluids into hydrocarbon-bearing rock formations. More specifically, the disclosure relates to laboratory methods for determining certain unconventional flow parameters to measure the imbibition over time of hydraulic fracturing fluids into a low-permeability hydrocarbon-bearing rock formation.

2. Description of the Related Art

Unconventional hydrocarbon shale gas resources present significant potential for meeting the world's ever increasing energy demand. Hydraulic fracturing of horizontal wells is a widely used technique for recovering natural gas from shale gas and other unconventional reservoirs, which are characterized in part by extremely low permeabilities. This hydrocarbon recovery method generally involves the use of large volumes of fracturing fluids along with proppants. Water-based fracturing fluids (that are currently most commonly used in hydraulic fracturing) comprise about 99% fresh or recycled water, complemented by the addition of chemicals like surfactants, friction reducers, biocides, clay stabilizers and scale inhibitors.

During hydraulic fracturing and the well shut-in stages in a shale gas reservoir, a significant amount of fracturing fluid will flow into surrounding shale formations through hydraulic fractures. A certain amount of the hydraulic fracturing fluids, oftentimes comprised mostly of water, will absorb into the shale rock, or other rock, in the hydrocarbon-bearing formation through a process referred to as "imbibition." This is known, because while certain amounts of fracking fluids are recovered from formations, large amounts of fracking fluids are lost in the formation. Spontaneous imbibition is of interest, because it is a mechanism for liquid uptake by the formation during the relatively long well shut-in period after flow-back of some fracturing fluids to the surface. One definition of imbibition includes a process by which one fluid, for example water, displaces another immiscible fluid, such as an immiscible hydrocarbon.

The process of imbibition has many practical implications for shale gas recovery. Liquid imbibition can cause the loss of gas relative permeability and lead to chemically altered zones near fracture-matrix interfaces in hydrocarbon-bearing formations. Imbibition of hydraulic fluids, such as water, into shale rock may reduce hydrocarbon recovery from a well. Darcy's law describes generally the flow of fluids through porous media. However, in part because of the strong solid-liquid interactions in low-permeability media, such as, for example, shale rock, Darcy's law is not always adequate for describing liquid flow patterns in a shale formation that become unconventional. "Tight" rock formations are those that are low-permeability, and include shale rock, tight carbonate, and tight sandstone.

Therefore, there is a need for accurate and efficient methods for measuring unconventional imbibition of fluids into low-permeability hydrocarbon-bearing formations where unconventional flow can be present.

SUMMARY

Described herein are methods for measuring and determining unconventional liquid imbibition of hydraulic fracturing fluids into low-permeability, hydrocarbon-bearing formations. In this disclosure, unconventional liquid flow behavior in low-permeability media is referred to as "unconventional flow behavior," because it does not obey Darcy's Law, and the term "non-Darcy flow" often has been used to describe fluid-flow behavior that deviates from Darcy's law as a result of high flow velocity in high-permeability media (and this situation does not apply here). The disclosure relates to laboratory methods for determining certain unconventional flow parameters to measure the imbibition over time of hydraulic fracturing fluids into a low-permeability hydrocarbon-bearing formation. Laboratory tests allow determination of a non-conventional flow index "n" and a transport parameter "$D(\theta)$" to accurately measure and determine liquid imbibition into a low-permeability hydrocarbon-bearing rock formation over time.

Therefore, disclosed herein is a method of determining a rate of fluid imbibition into a low-permeability, hydrocarbon-bearing rock matrix. The method includes the steps of preparing a sample obtained from the low-permeability, hydrocarbon-bearing rock matrix for a spontaneous imbibition test with a fluid, the fluid operable for use in hydraulic fracturing of the low-permeability, hydrocarbon-bearing rock matrix and conducting the spontaneous imbibition test on the sample. The method further includes the steps of recording cumulative imbibition of the fluid into the sample over time, determining an unconventional flow index, the unconventional flow index representing unconventional flow, and the unconventional flow index being responsive to a relational assumption where liquid flux into the sample causing the cumulative imbibition is a power function of a pressure gradient of the sample, and measuring volumetric liquid content spatial distribution along the sample after the spontaneous imbibition test.

The method also includes the steps of determining a transport parameter of the sample responsive to (1) the volumetric liquid content spatial distribution along the sample after the spontaneous imbibition test, (2) an initial liquid content of the sample before the spontaneous imbibition test, and (3) the unconventional flow index, and determining the rate of fluid imbibition into the low-permeability, hydrocarbon-bearing matrix over time responsive to the unconventional flow index and the transport parameter.

In some embodiments of the method, the sample is selected from the group consisting of shale, tight carbonate, and tight sandstone. In other embodiments, the sample comprises shale. In some embodiments, the step of preparing the sample further comprises the steps of forming the sample into a column shape with a length L and a uniform cross section through the length L, the sample having a fluid-contacting portion, non-fluid-contacting portions, and an upper air flow portion, minimizing evaporation sources from the non-fluid-contacting portions of the sample, and allowing air flow at the upper air flow portion of the sample.

In some embodiments, the step of conducting the spontaneous imbibition test on the sample proceeds for between about 1 minute and about 20 hours, or for between about 1 minute and about 2 hours, or for between about 1 hour and about 10 hours, or for between about 5 hours and about 20 hours. In some embodiments, the step of recording cumulative imbibition of the fluid into the sample over time includes the step of recording the mass of the sample at time intervals during the spontaneous imbibition test to compose recorded sample mass data for recorded time data. In other embodiments, the step of determining an unconventional flow index further comprises the steps of creating a plot by plotting log data of the recorded sample mass data versus log data of the recorded time data, fitting a line to the plot, and calculating the unconventional flow index, where the line has a slope equal to 1/(n+1), and where n is the unconventional flow index.

In some embodiments, the step of measuring volumetric liquid content spatial distribution along the sample after the spontaneous imbibition test is performed by nuclear magnetic resonance. In other embodiments, the step of determining a transport parameter of the sample responsive to the volumetric liquid content spatial distribution along the sample after the spontaneous imbibition test further comprises the steps of averaging the spatial distribution of liquid content along the sample over a cross section of the sample to obtain spatial distribution of liquid content data and smoothing the spatial distribution of liquid content data to remove noisy data.

Sill in other embodiments, the step of smoothing is performed by a method selected from the group consisting of utilizing one or more fitting parameters and utilizing a smoothing spline function.

In some embodiments, the step of determining the rate of fluid imbibition into the low-permeability, hydrocarbon-bearing rock matrix over time responsive to the unconventional flow index and the transport parameter further comprises the step of calculating liquid content per time by the equation $$\frac{\partial \theta}{\partial t} = -\frac{\partial q}{\partial x} = \frac{\partial}{\partial x}\left(D(\theta)\left|\frac{\partial \theta}{\partial x}\right|^{n-1}\frac{\partial \theta}{\partial x}\right),$$

where θ is liquid content, t is time, q is liquid flux, D(θ) is the transport parameter, and n is the unconventional flow index.

BRIEF DESCRIPTION OF THE DRAWINGS

So that the manner in which the recited features, aspects and advantages of the disclosure, as well as others that will become apparent, are attained and can be understood in more detail, a more particular description of certain embodiments briefly summarized above can be had by reference to the embodiments that are illustrated in the drawings that form a part of this specification. It is to be noted, however, that the appended drawings illustrate only exemplary embodiments and are, therefore, not to be considered limiting of the disclosure's scope, for the disclosure can admit to other equally effective embodiments.

DETAILED DESCRIPTION OF THE EXEMPLARY EMBODIMENTS

Figure 1:
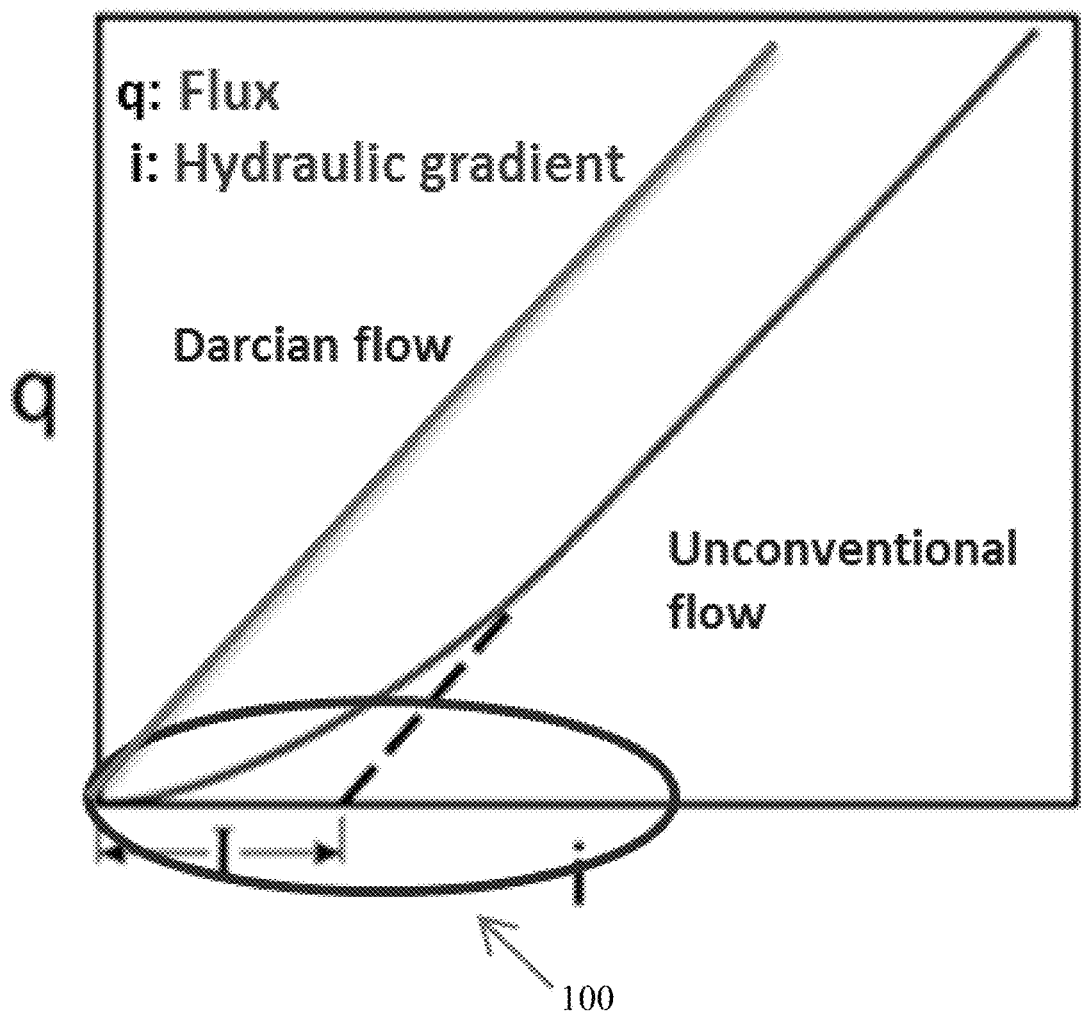
FIG. 1 is a graph showing flux vs. hydraulic gradient for a Darcian flow regime, under Darcy's Law, and for an unconventional flow regime in a low-permeability medium.

Referring first to FIG. 1, a graph showing flux vs. hydraulic gradient for a Darcian flow regime, under Darcy's Law, and for an unconventional flow regime into a low-permeability medium is shown. Fluid flow in porous media is traditionally described by Darcy's law. Darcy's law is based on the correlation that water flux is directly proportional to the hydraulic gradient in fluid flow through certain porous media. However, it has been shown that Darcy's law is not always adequate for describing low-permeability media. For example, it has been reported that water flux in a low-permeability clay soil is proportional to a power function of the hydraulic gradient when the gradient is less than a critical value, whereupon the relationship between water flux and gradient becomes linear for large gradient values.

It has been posited that a certain hydraulic gradient is required to overcome the maximum binding energy of mobile pore water. From experimental results, Miller and Low (Miller, R. J., and Low P. F., 1963. Threshold gradient for water flow in clay systems. Soil. Sci. Soc. Am. Proc. 27(6), 605-609) found the existence of a hydraulic gradient below which water is essentially immobile. After analyzing several data sets for water flow in clay soils, Swartzendruber (Swartzendruber, D. 1961. Modification of Darcy's law for the flow of water in soils. Soil Science 93: 22-29. Soil. Sci. Soc. Am. J. 69, 328-342) proposed a modified Darcy's law in which non-linear behavior of water flux vs. gradient is described by an exponential function.

Zou (Zou, Y., 1996. A non-linear permeability relation depending on the activation energy of pore liquid. Geotechnique 46(4), 769-774) developed a nonlinear flux-gradient relationship depending on the activation energy of pore liquid. Zou assumed that the activation energy of pore water in clay is not only variable with the distance from the solid particle surface, but also with the flow velocity of pore water. The model, which includes several empirical parameters, is able to fit a number of data sets that show nonlinear flux-gradient relationships at low hydraulic gradients and linear relationships at high gradients.

Xu et al. (Xu, S. L., Yue, X. A., Hou, J. R., 2007. Experimental investigation on flow characteristics of deionized water in microtubes. Chinese Science Bulletin 52(6): 849-854) experimentally investigated the relationship between flux of deionized water and hydraulic gradient in individual micro-tubes with diameters ranging from 2 to 30 μm. Experiments demonstrated that water flow in micro-tubes with diameters of larger than 16 μm is consistent with Darcy's law, but not for smaller diameters. In the latter cases, the relationship between water flux and hydraulic gradient becomes non-linear.

Liu (Liu, H. H., 2014. Non-Darcian flow in low-permeability media: Key issues related to geological disposal of high-level nuclear waste in shale formations. Hydrogeology Journal, DOI 10.1007/s10040-014-1145-x.) reviewed studies on unconventional liquid flow in shale formations within the context of nuclear waste geological disposal and indicated that unconventional flow exists in low-permeability media. Shale has been considered a rock type for high-level nuclear waste disposal by a number of countries. The imbibition process in shale gas reservoirs is complex, in part, because it involves two-phase flow.

Research has demonstrated that the cumulative liquid mass of imbibition into shale samples (from spontaneous imbibition laboratory tests) as a function of time generally does not follow a straight line with a slope of 0.5 in log-log plots (Hu, Q. H., and R. P. Ewing, 2014. Integrated experimental and modeling approaches to studying the fracture-matrix interaction in gas recovery from Barnett shale. Report 09122-12. University of Texas at Arlington; Roychaudhuri R., Tsotsis, T. T. and Jessen, K., 2013. An experimental investigation of spontaneous imbibition in gas shales. Journal of Petroleum Science and Engineering 111: 87-97). A straight line with a slope of 0.5 in log-log plots is a signature of Darcy's flow.

Still referring to FIG. 1, a straight line corresponds to Darcy's flow. Unconventional liquid flow behavior, however, has not been given sufficient attention in modeling fluid flow in shale gas reservoirs. In some embodiments of the present disclosure, a phenomenological model is developed for unconventional liquid imbibition processes, in some embodiments into hydrocarbon-bearing formations including, but not limited to, shale rock and other tight rock formations such as tight carbonate and tight sandstone. In some embodiments, a methodology is proposed to estimate values for the associated model parameters from laboratory tests.

Relationships Between Liquid Flux and Hydraulic Gradient

In the discussions of equations presented herein, the following variables represent the following associated properties, unless indicated otherwise in particular circumstances: A=the cross sectional area of a shale column (m$^2$); D=a variable defined in Equation 12 (m$^{n+1}$/s); g=gravitational acceleration (m/s$^2$); i=hydraulic gradient (dimensionless); I=threshold gradient (dimensionless); I*=a parameter defined in Equation 9-1 (dimensionless); $i_1$=a parameter in Equation 3 (dimensionless); K=hydraulic conductivity (m/s); k=permeability (m$^2$); k'=a parameter in Equation 3 (m/s); $k_r$*=an analog of relative permeability for liquid flow (Equation 10) (m$^{1+n}$Pa$^{1-n}$); M=cumulative imbibition (kg); N=a parameter in Equation 3 (dimensionless); n=a positive parameter in Equation 10 (dimensionless); $p_c$=capillary pressure (Pa); q=liquid flux (m/s); t=time (s); x=location within a shale column (m); α=a positive constant in Equation 7 (dimensionless); α'=a fitting parameter in Equation 23 (dimensionless); β=a fitting parameter in Equation 23 (m/s$^{1/(n+1)}$); λ=a transform variable defined in Equation 17 (m/s$^{1/(n+1)}$); μ=liquid viscosity (Pa·s); ρ=liquid density (kg/m$^3$); θ=liquid content (dimensionless); $θ_i$=initial liquid content (dimensionless); $θ_0$=liquid content at x=0 (dimensionless); θ*=dimensionless liquid content (Equation 24).

Unconventional flow behavior can be described by the relationship between liquid flux and an associated hydraulic gradient (or pressure gradient when gravity effects can be ignored). Relationships for liquid flow in clay media can be used, in some embodiments, to accurately describe fracturing-fluid flow in shale formations. The flux-gradient relationship in Darcy's law is given by Equation 1 as follows:

$$q = Ki \qquad \text{Eq. 1}$$

In Equation 1, q (m/s) is liquid flux, K (m/s) is hydraulic conductivity and i (–) is hydraulic gradient. The relationship of Equation 1 is shown graphically in FIG. 1. Here, Equation 1 includes only magnitudes of variables for one-dimensional flow and therefore q, K, and i are all positive. A similar treatment, for convenience, is used for all the other relationships to be discussed in this section for relationships between liquid flux and hydraulic gradient.

The hydraulic conductivity K is related to permeability, k, by Equation 2 as follows:

$$K = \frac{k\rho g}{\mu} \qquad \text{Eq. 2}$$

In Equation 2, g is gravitational acceleration, and ρ and μ are liquid density and viscosity, respectively. In some embodiments, the conditions under which flow regimes are measured or determined are isothermal conditions.

Darcy's law was initially developed for water flow in saturated porous media. Buckingham (Buckingham, E. 1907. Studies on the movement of soil moisture. Bulletin 38. USDA Bureau of Soils, Washington, D.C.) extended Darcy's law to unsaturated conditions. Buckingham used an unsaturated hydraulic conductivity, a function of water saturation, to replace hydraulic conductivity in Darcy's law. Liu (Liu, H. H., 2011. A conductivity relationship for steady-state unsaturated flow processes under optimal flow conditions. Vadose Zone Journal 10(2), 736-740; Liu, H. H., 2014. A thermodynamic hypothesis regarding optimality principles for flow processes in geosystems. Chinese Science Bulletin, 59(16) 1880-1884) has made an effort to extend the Darcy-Buckingham law to a case involving fingering flow.

A relationship between liquid flux and hydraulic gradient has been proposed by Hansbo (Hansbo, S. 1960. Consolidation of clay, with special reference to influence of vertical sand drains. Swed. Geotech. Inst. Proc. 18, Stockholm. Hansbo, S., 2001; Consolidation equation valid for both Darcian and non-Darcian flow. Geotechnique 51(1), 51-54) to consider the unconventional flow behavior in clay media, shown as follows in Equations 3-1 to 3-3:

$$q = k'i^N \text{ for } i \leq i_1 \qquad \text{Eq. 3-1}$$

$$q = k'Ni_1^{N-1}(i - I) \text{ for } i \geq i_1 \qquad \text{Eq. 3-2}$$

$$i_1 = \frac{IN}{(N-1)} \qquad \text{Eq. 3-3}$$

The formulation of Hansbo includes three parameters k' (m/s), N (–) and I (–). Here, k' is not the hydraulic conductivity and Equation 3-2 corresponds to a linear function between liquid flux and hydraulic gradient i.

Still referring to FIG. 1 and Equations 3-1 to 3-3, parameter I is called the "threshold gradient" herein, and refers to the intersection between the i axis and the linear part of the relationship. This is shown within the circled region 100 of FIG. 1. Hansbo demonstrated that Equations 3-1 to 3-3 can fit related experimental observations, and developed a theoretical approach to dealing with clay consolidation processes. However, as indicated by Swartzendruber, cited previously, Equations 3-1 to 3-3 consist of two separate mathematical expressions and three related parameters, which cannot be evaluated unless data are available all the way from i=0 out to and including an appreciable part of the linear portion of the flux-gradient curve.

To overcome the difficulties encountered in applying Equations 3-1 to 3-3, Swartzendruber introduced a new version of the modified Darcy's law based on a relation for dq/di, shown by Equation 4:

$$\frac{dq}{di} = K(1 - e^{-i/I}) \quad \text{Eq. 4}$$

In Equation 4, for a large value of hydraulic gradient i, dq/di approaches a constant K, that is hydraulic conductivity. Integrating Equation 4, and using q=0 at i=0, this leads to Equation 5 as follows:

$$q = K[i - I(1 - e^{-i/I})] \quad \text{Eq. 5}$$

Equation 5 involves two parameters, K and I. The equation of Swartzendruber has been evaluated with a number of collected data sets, and satisfactory agreement has generally been obtained in most cases between Equation 5 and the data. However, Equation 5 fails to capture the full range of unconventional flow behavior under different conditions.

Another flux-gradient relationship for low-permeability media has been proposed by Bear (Bear, J., 1979. Hydraulics of Groundwater. McGraw-Hill, Inc., New York.) represented by Equations 6-1 to 6-2, shown as follows:

$$q = 0 \text{ for } i \leq I \quad \text{Eq. 6-1}$$

$$q = K(i - I) \text{ for } i \geq 1 \quad \text{Eq. 6-2}$$

Similar to Equation 5, Equations 6-1 and 6-2 involve only two parameters (K and I) and are mathematically simpler than other relationships. Equations 6-1 and 6-2, however, cannot adequately capture the flow behavior (or non-linear flux-gradient relationship) at low i values. Therefore, Equations 6-1 and 6-2 should be applied only when i is large. Equation 6-2 is a limiting case of Equation 5 for i/I→∞.

Liu and Birkholzer (Liu, H. H. and Birkholzer, J., 2012. On the relationship between water-flux and hydraulic gradient for unsaturated and saturated clay. Journal of Hydrology, 475, 242-247) proposed to generalize Swartzendruber's relationship by using Equation 7 as follows:

$$\frac{dq}{di} = K\left(1 - e^{-\left(\frac{i}{I^*}\right)^\alpha}\right) \quad \text{Eq. 7}$$

In Equation 7, $\alpha$ is a positive constant, and $I^*$ is a parameter related to $\alpha$ and I. For $\alpha=1$, Equation 7 is reduced to Equation 4. For $\alpha \to \infty$, $$\frac{dq}{di} \to 0$$

when $$\frac{i}{I^*} < 1,$$

and $$\frac{dq}{di} \to K$$

when $$\frac{i}{I^*} > 1.$$

In this case, Equation 7 essentially represents the flux-gradient behavior given in Equation 6. Thus, with one more parameter ($\alpha$), Equation 7 can capture a relatively large range of unconventional flow behavior.

Integrating Equation 7 with the condition of q=0 at i=0 yields Equation 8 as follows:

$$q = K\left[i - \frac{I}{\gamma\left(\frac{1}{\alpha}\right)}\gamma\left(\frac{1}{\alpha}, \left(\frac{i}{I^*}\right)^\alpha\right)\right] \quad \text{Eq. 8}$$

where I is given by Equation 9-1 as follows:

$$I = \frac{I^*}{\alpha}\gamma\left(\frac{1}{\alpha}\right) \quad \text{Eq. 9-1}$$

and $\gamma$ refers to Gamma functions as shown in Equations 9-2 and 9-3 as follows:

$$\gamma(a, y) = \int_0^y T^{a-1} e^{-T} dT \quad \text{Eq. 9-2}$$

$$\gamma(a) = \int_0^\infty T^{a-1} e^{-T} dT \quad \text{Eq. 9-3}$$

As previously indicated, unconventional flow behavior likely is determined, at least in part, by the degree of solid-liquid interaction within a low permeability formation. A stronger interaction should correspond to a small pore size (or low permeability) and large threshold gradient (I). Without being bound by any theory or principle, it is believed that a correlation between permeability and I exists.

A Phenomenological Model of Fluid Imbibition into Hydrocarbon-Bearing Formations The relationships presented above are deficient in providing accurate and efficient means for measuring imbibition into low-permeability hydrocarbon-bearing formations, at least because laboratory determination of related parameters in these relationships requires measurement of fluid flux as a function of pressure gradient under different two-phase flow conditions. Such measurement of fluid flux is very difficult, if not impossible, given the fact that shale has extremely low permeability. Thus, herein presented is a model that is phenomenological in nature, consistent with the relationships discussed above, and consistent with related experimental observations. Some embodiments of the present disclosure allow for establishing a straightforward laboratory procedure to determine key parameters associated with unconventional liquid flow in low-permeability media.

As noted above, spontaneous imbibition is of particular interest, because it is a significant mechanism for liquid uptake by hydrocarbon-bearing formations during relatively long well shut-in periods before flow-back starts with hydrocarbons flowing to the surface. In some embodiments of the present disclosure, imbibition that is driven by the capillary force is measured and determined by laboratory means.

In some embodiments of the present disclosure, liquid flux in a low-permeability medium is modeled as a power function of the capillary pressure gradient, shown by Equation 10 as follows:

$$q = -\frac{k_r^*}{\mu} \left| \frac{\partial p_c}{\partial x} \right|^{n-1} \frac{\partial p_c}{\partial x} \qquad \text{Eq. 10}$$

In Equation 10, $k_r^*$ is an analog of relative permeability for liquid flow, $p_c$ is capillary pressure (that is negative), n is a positive parameter called the unconventional flow index, x is location within a shale, or other tight rock, sample column, and $\mu$ is fluid viscosity. Equation 10 will be reduced to Darcy's law for n=1. The liquid flux q can be positive or negative to represent its direction. In the previous section, q represents the magnitude of liquid flux only.

Figure 2:
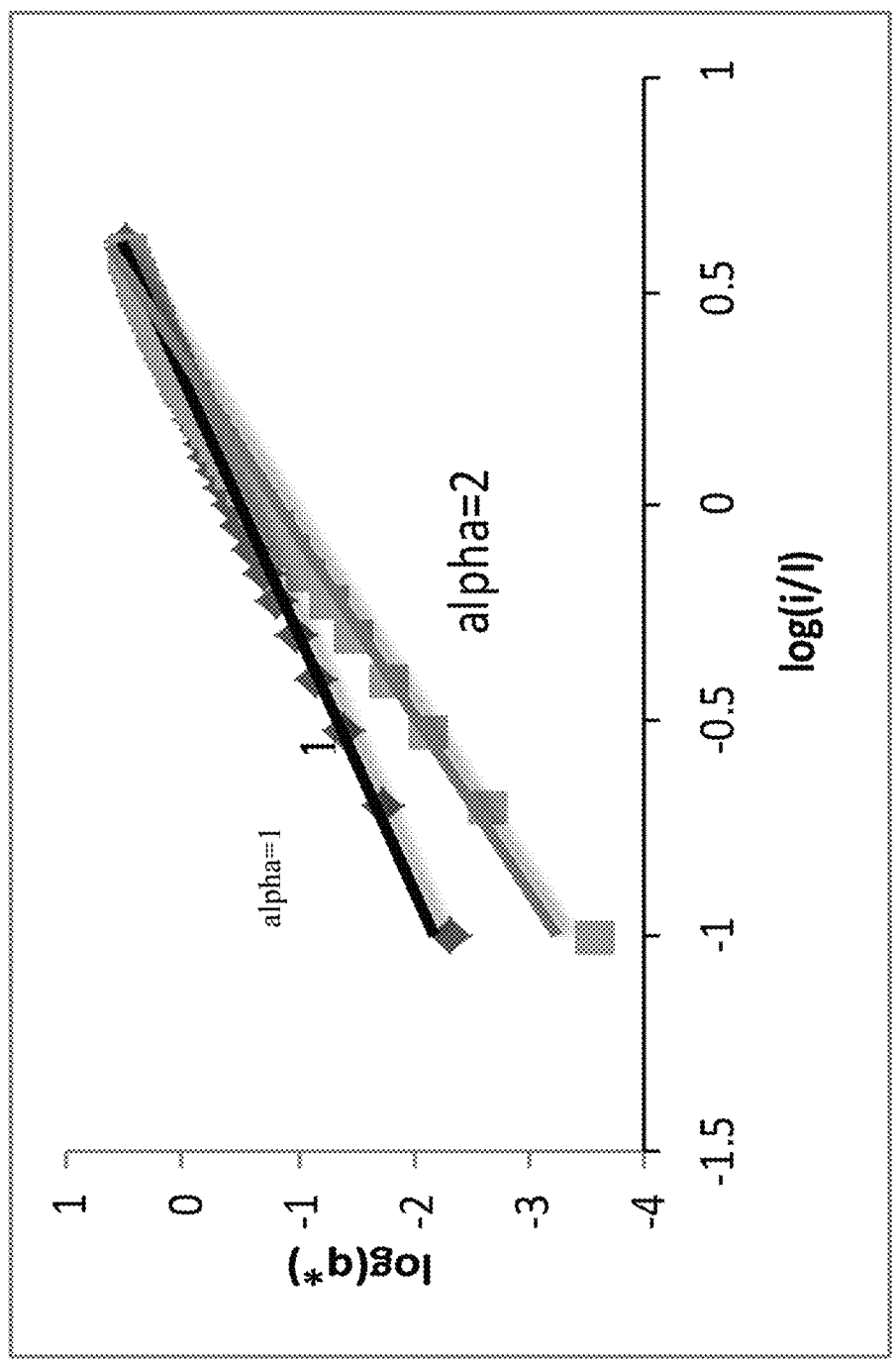
FIG. 2 is a graph showing the approximation of Equation 8 by power functions for i/I<4.

Referring now to FIG. 2, a graph showing the approximation of Equation 8 by power functions for i/I<4 is shown. In FIG. 2, q* is defined as magnitude of q divided by KI, as calculated from Equation 8. One assumption of Equation 10 is that liquid flux is a power function of the capillary pressure gradient in low-permeability mediums. Such an assumption is justified by the following two considerations. First, as shown in FIG. 2, Equation 8 can be approximately represented by a power-law function for a large range of hydraulic gradient (i/I<4), that is capillary pressure gradient divided by fluid density and by gravitational acceleration. Second, this treatment is consistent with spontaneous imbibition observations, as will be shown in the Experiments described as follows.

During the imbibition process, a unique relationship between capillary pressure and volumetric liquid content $\theta$ exists. Such a relationship is shown by Equation 11 as follows:

$$\frac{\partial p_c}{\partial x} = \frac{dp_c}{d\theta} \frac{\partial \theta}{\partial x} \qquad \text{Eq. 11}$$

Using Equation 11, Equation 10 from above can be rewritten as Equation 12, shown as follows:

$$q = -D(\theta) \left| \frac{\partial \theta}{\partial x} \right|^{n-1} \frac{\partial \theta}{\partial x} \qquad \text{Eq. 12}$$

In Equation 12, q is the flux of the liquid flow, $\theta$ is volumetric liquid content, n is a positive parameter called the unconventional flow index, and x is location within a shale, or other tight rock, column sample. When n is 1, Equation 12 is reduced to conventional Darcy's law. Herein, $D(\theta)$ from Equation 12 is referred to as a "transport parameter," and can be represented as shown in Equation 13:

$$D(\theta) = \frac{k_r^*}{\mu} \left| \frac{dp_c}{d\theta} \right|^n \qquad \text{Eq. 13}$$

When Equation 12 is substituted for q in $$-\frac{\partial q}{\partial x},$$

this yields Equation 14, shown as follows:

$$\frac{\partial \theta}{\partial t} = -\frac{\partial q}{\partial x} = \frac{\partial}{\partial x}\left(D(\theta)\left|\frac{\partial \theta}{\partial x}\right|^{n-1}\frac{\partial \theta}{\partial x}\right) \qquad \text{Eq. 14}$$

Certain embodiments of the present disclosure focus on a one-dimensional flow case, because the imbibition process can be considered one-dimensional. Penetration depth of fracturing fluids into a shale matrix is generally small as a result of low shale permeability. In order to use Equation 14 to simulate liquid flow, values for the parameter n, "unconventional flow index," and the parameter $D(\theta)$, "the transport parameter," are needed. Herein presented is a solution to Equation 14, which can serve as a basis for experimentally determining the parameters n and $D(\theta)$ in the laboratory with hydrocarbon-bearing formation samples.

Figure 3:
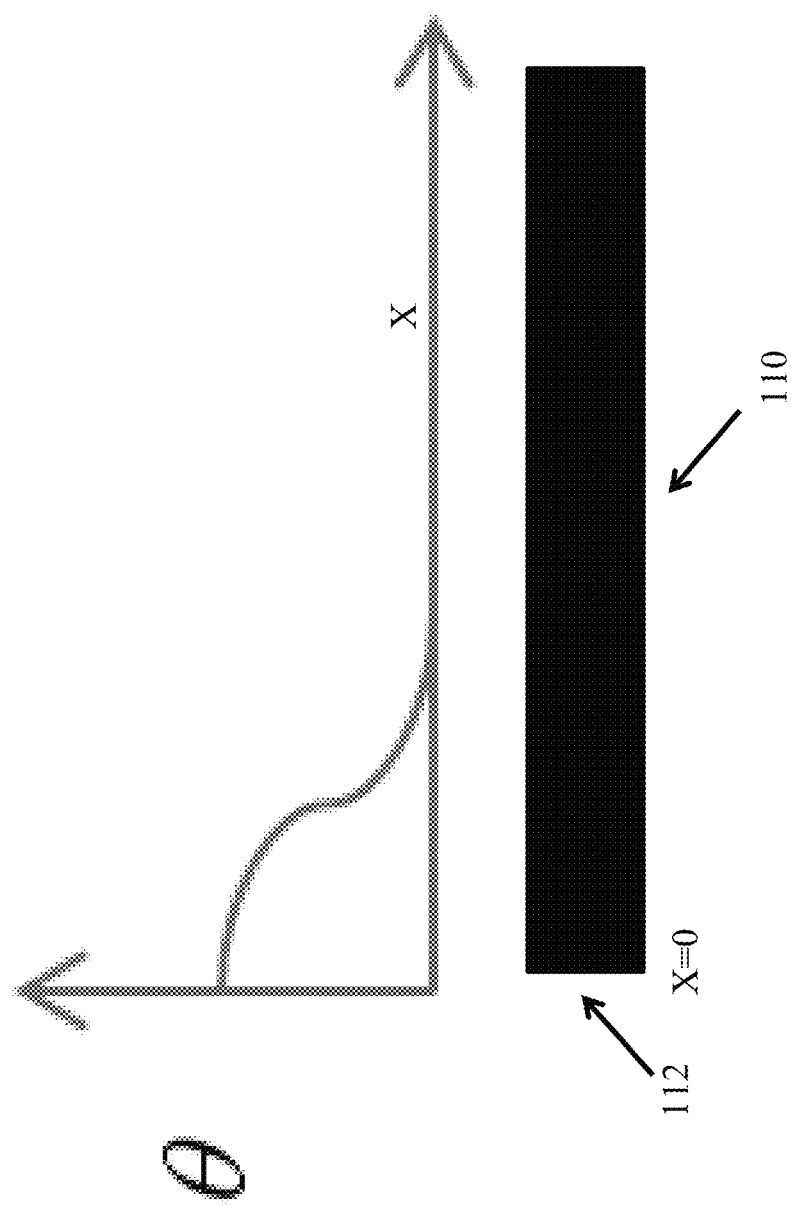
FIG. 3 is a graphical representation of a shale column subject to the imbibition process.

Referring now to FIG. 3, a graphical representation of a shale column subject to the imbibition process is shown. Shale sample column 110 has a first end 112, which is the end contacting a fluid reservoir at location x=0. For example, in one embodiment, an infinitely long shale column is subject to the imbibition process (from the inlet x=0) and the following boundary and initial conditions shown in Equations 15-1 to 15-3 apply:

$$\theta(x,t)=\theta_i \ (x \geq 0, t=0) \qquad \text{Eq. 15-1}$$

$$\theta(x,t)=\theta_0 \ (x=0, t>0) \qquad \text{Eq. 15-2}$$

$$\theta(x,t)=\theta_i \ (x \to \infty, t>0) \qquad \text{Eq. 15-3}$$

In certain embodiments, the liquid content gradient is negative. Thus, Equation 14 can be rewritten as Equation 16, shown as follows:

$$\frac{\partial \theta}{\partial t} = -\frac{\partial}{\partial x}\left(D(\theta)\left|\frac{\partial \theta}{\partial x}\right|^n\right) \qquad \text{Eq. 16}$$

Equation 17 provides a useful transformation equation as follows:

$$\lambda = xt^{-\frac{1}{n+1}} \qquad \text{Eq. 17}$$

With equations 16 and 17, these can be combined and rewritten as Equations 18-1, 18-2, and 19 as follows:

$$\theta(\lambda) = \theta_i \quad (\lambda \to \infty) \qquad \text{Eq. 18-1}$$

$$\theta(\lambda) = \theta_0 \quad (\lambda = 0) \qquad \text{Eq. 18-2}$$

-continued $$\frac{\lambda}{n+1}\frac{d\theta}{d\lambda} = \frac{d}{d\lambda}\left[D(\theta)\left|\frac{d\theta}{d\lambda}\right|^n\right]$$ Eq. 19

Equations 16 and 19 are equivalent; however, Equation 19 can be much more easily solved than Equation 16, because Equation 19 is an ordinary differential equation with $\lambda$ as the only independent variable. Directly integrating Eq. 19 for the interval ($\lambda$, $\infty$) yields Equation 20, shown as follows:

$$D(\theta) = \frac{\int_{\theta_i}^{\theta}\frac{\lambda}{n+1}d\theta}{\left|\frac{d\theta}{d\lambda}\right|^n}$$ Eq. 20

Equation 20 shows that $D(\theta)$ can be calculated when $\theta(\lambda)$ is given. Based on liquid continuity, cumulative imbibition (in terms of liquid volume) can be calculated as shown in Equation 21:

$$V(t) = A\int_0^\infty (\theta - \theta_i)dx = A(\theta - \theta_i)x\Big|_0^\infty - A\int_{\theta_0}^{\theta_i} xd\theta = A\int_{\theta_i}^{\theta_0} xd\theta$$ Eq. 21

In Equation 21, A is cross-sectional area of the shale column. By combining Equations 21 and 17, this provides Equation 22, shown as follows:

$$V(t) = \left(A\int_{\theta_i}^{\theta_0}\lambda d\theta\right)t^{\frac{1}{n+1}}$$ Eq. 22

Thus, the cumulative volume is a power function of time. For Darcian flow in which n=1, the exponent $1/(n+1)$ is equal to 0.5. For unconventional liquid flow, the exponent is no longer 0.5 (see FIG. 4), but is determined using methods of the present disclosure. While Equations 21 and 22 have been discussed in terms of cumulative volume, cumulative mass can be quickly calculated using $\rho$ for water-based liquid density, assumed to be a constant 1 g/cm$^3$, in some embodiments.

Figure 7:
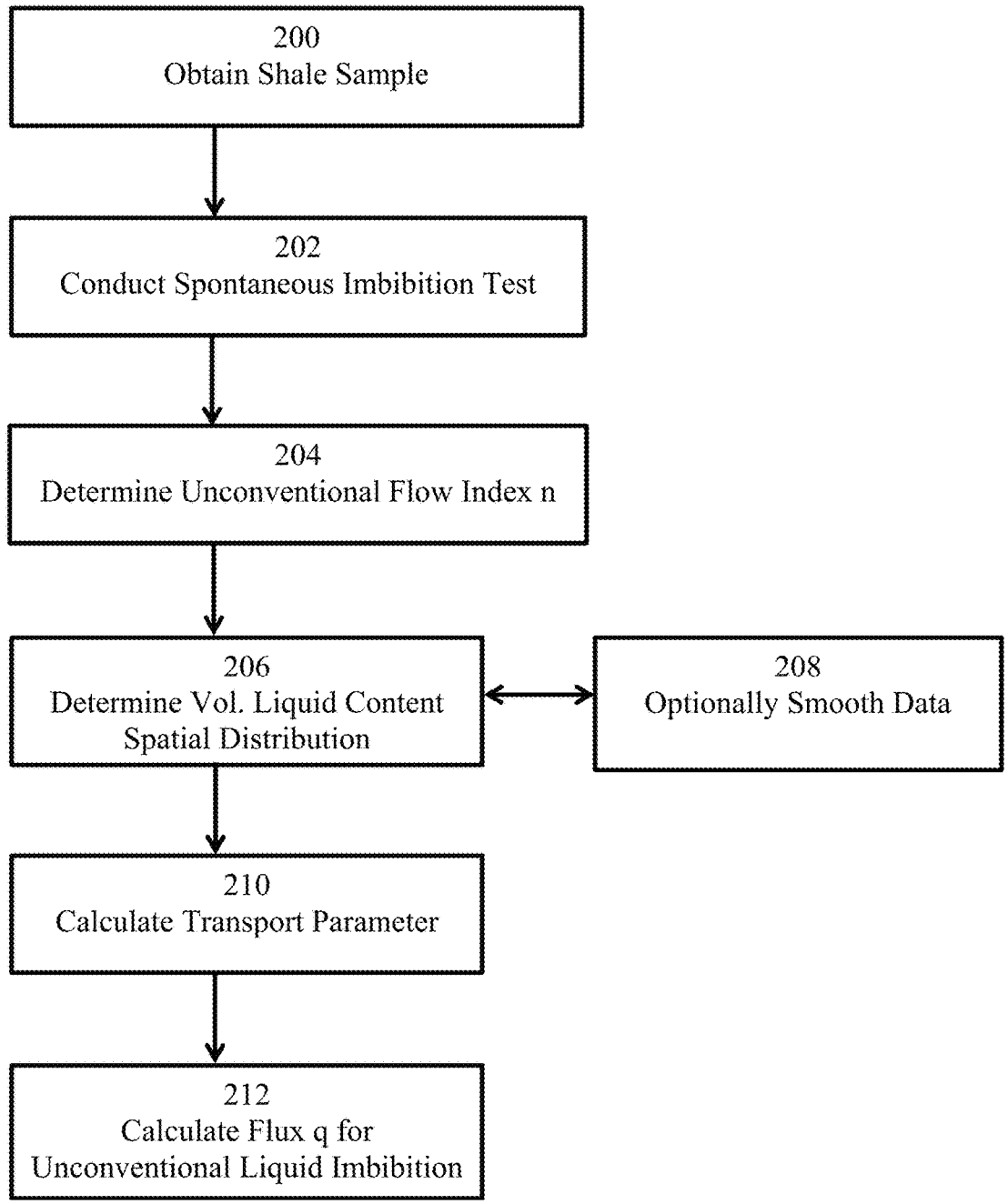
FIG. 7 is a flow chart for one embodiment of a method for determining an unconventional flow index n and a transport parameter D(θ).

In some embodiments of the present method, then, liquid flux, unlike the commonly used Darcy's law, is proportional to a power function of capillary pressure (or liquid content) gradient according to Equations 10 and 12. Referring to FIG. 7, the unconventional flow index n and transport parameter $D(\theta)$ are determined using steps represented graphically by the flow chart. Briefly, the flow index n is determined using observed cumulative imbibition into a shale core, and the transport parameter is estimated by measuring the spatial distribution of liquid content along a shale core (with the specially designed boundary and initial conditions described in Equations 15-1 to 15-3 described above), measured by high-resolution methods, in some embodiments nuclear magnetic resonance ("NMR").

Still referring to FIG. 7, a flow chart for one embodiment of a method for determining an unconventional flow index n and a transport parameter $D(\theta)$ is shown. First, at step 200 one or more samples are obtained for a medium that is of interest for determining a rate of imbibition per time. For example, one or more samples of shale rock might be obtained from a hydrocarbon-bearing formation in which hydrocarbon recovery, with or without hydraulic fracturing, is currently active, planned in the future, or expired. Other tight rock formations may include tight carbonate and tight sandstone.

An obtained sample already may have experienced imbibition of hydraulic fracturing fluids during a hydraulic fracturing process, such as during well shut-in, or a sample may be from a formation in which hydrocarbon recovery processes have not begun. Any type of hydrocarbon-bearing formation sample at any stage before, during, or after hydrocarbon recovery is envisioned for use in the methods of the present disclosure.

Figure 4:
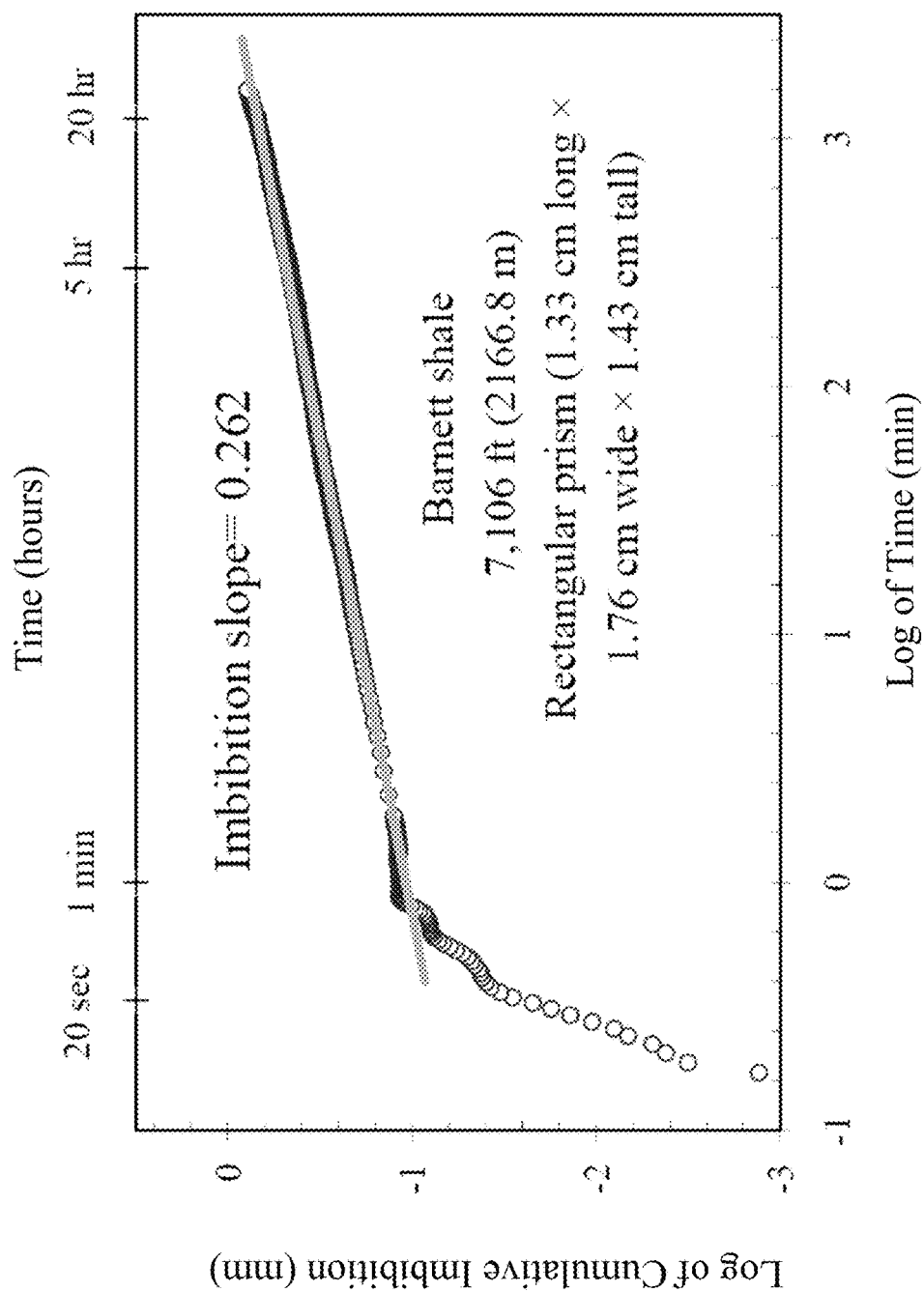
FIG. 4 is a graph showing observed cumulative imbibition as a function of time for a Barnett shale sample (from Hu and Ewing 2014, cited herein).
Figure 5:
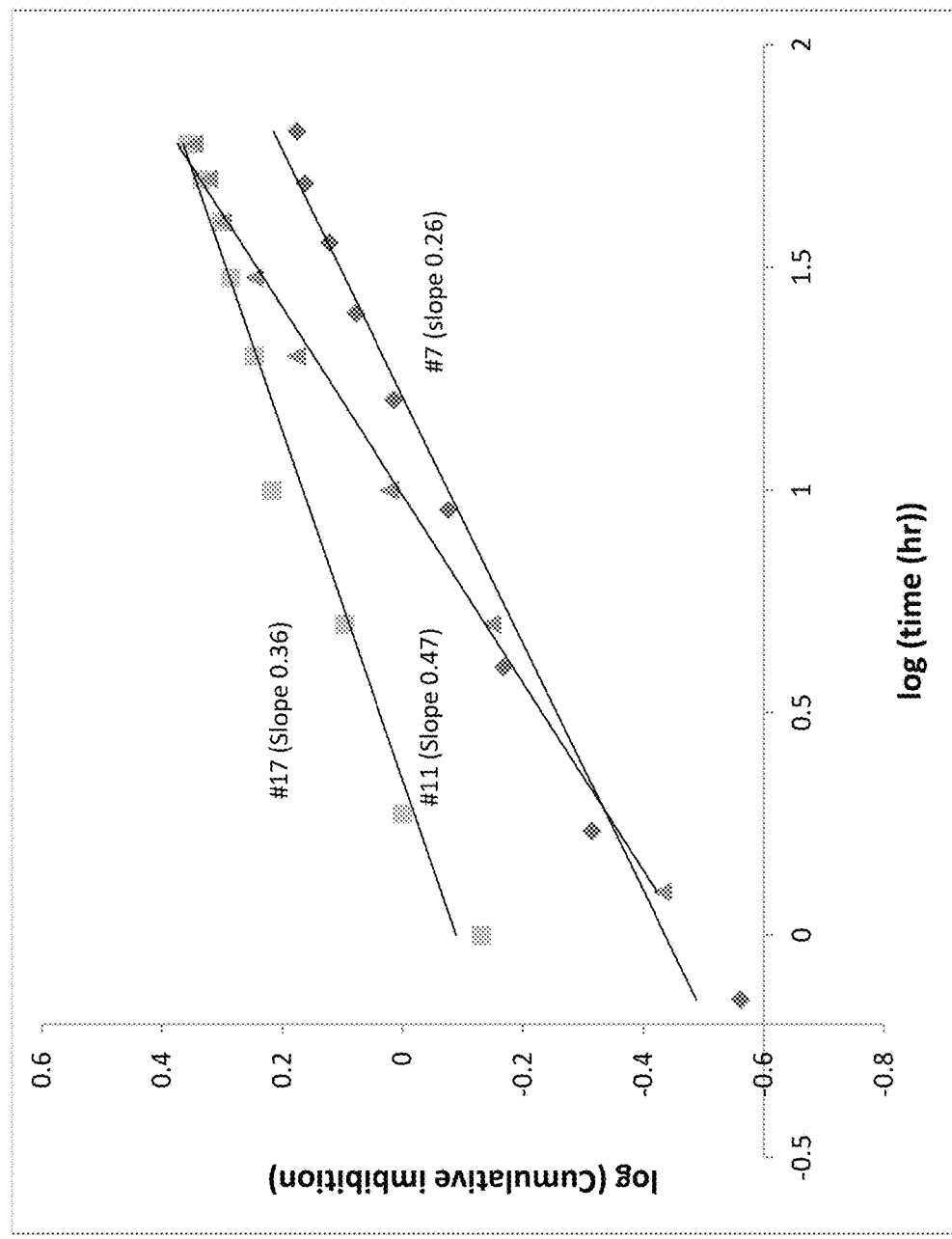
FIG. 5 is a graph showing imbibition data of Roychaudhuri et al. (cited herein) and lines fit to the data used to determine the unconventional flow index "n."

At step 202, a spontaneous imbibition test for the one or more samples is performed to collect cumulative imbibition data. Cumulative imbibition is referred to previously as "V(t)," where the cumulative imbibition is a function of time "t." This is shown by Equation 22. In one embodiment, the bottom face of a sample in the form of a column can be submerged to a depth between about 0.5 mm and about 5 mm in a fluid reservoir. The column can be any suitable shape, such as, for example, a cylinder or rectangular prism. In some embodiments, the bottom face of the column is submerged to a depth of about 1 mm in a fluid reservoir. Care should be taken to minimize evaporation from surfaces of the sample other than the "top" face or the face directly opposite the submerged bottom face. Cumulative imbibition volume, V, can be monitored by automatically recording the sample's mass over time t, and converting to volume using the density of the fluid. Exemplary data for cumulative imbibition versus time is shown in FIGS. 4 and 5.

At step 204, the unconventional flow index n is determined using Equation 22. As described previously, by fitting the data points from the spontaneous imbibition test plotted according to the log of cumulative imbibition versus the log of time with Equation 22, the slope of the fit line is equal to $1/(n+1)$. For Darcian flow in which n=1, the exponent $1/(n+1)$ is equal to 0.5. For unconventional liquid flow, the exponent is no longer 0.5. For example, in FIG. 4 where the imbibition slope is 0.262, the value for n is 2.8, which is significantly different from Darcian flow.

At step 206, after the spontaneous imbibition test and calculation of the unconventional flow index n, volumetric liquid content spatial distribution along the sample, referred to herein as $\theta(x)$, is determined using any suitable means. NMR can provide suitable measurements for volumetric liquid content spatial distribution over time; however, any other suitable, high-resolution means can be used. In step 206, the spatial distribution of liquid content is averaged over the cross section of the sample along the longitudinal direction of the sample, shown as $\theta(x)$ in FIG. 3, using NMR and/or other techniques that can provide liquid content measurement with resolution of 1 mm or less.

Measuring the volumetric liquid content spatial distribution along the shale sample provides ($\theta(x)$), liquid content at certain locations in the sample, at times (t). Afterward, $\theta$ as a function of $\lambda$ is required. Referring to Equations 17-19, $\lambda$, a transformation variable, is calculated using $$\lambda = xt^{-\frac{1}{n+1}}.$$

As explained above, this allows for the calculation of Equation 20, which provides the transport parameter $D(\theta)$.

The time t at which the spontaneous imbibition test ended is recorded and used for calculations in step 206 and in optional step 208.

Step 208 is an optional step, for execution in combination with step 206. For many practical reasons, an observed volumetric liquid content spatial distribution θ is often not smooth and involves certain degrees of fluctuation, which may in some embodiments cause some problems with calculating D(θ) from Eq. 20 when directly observed θ(λ) (or λ(θ)) is employed. The observed θ can be noisy because of measurement errors. In certain embodiments, smoothing treatment of the data is needed.

Since θ distributions generally follow certain regular shapes, a number of empirical algebraic expressions for θ(λ) exist and can be used to fit observed θ(λ) data adequately (e.g., Brutsaert W., 1982. Some exact solutions for non-linear desorptive diffusion. Journal of Applied Mathematics and Physics 33: 540-546; Evangelides C., Arampatzis G., and Tzimopoulos C., 2010. Estimation of soil moisture profile and diffusivity using simple laboratory procedures. Soil Science 175(3): 118-127). These expressions correspond to smooth curves. Furthermore, these expressions allow for derivation of algebraic expressions for D(θ) that are convenient to use in modeling studies.

To demonstrate the usefulness of the treatment discussed above, Equation 23 provides an expression for λ(θ) as follows:

$$\lambda = \beta(1-\theta^{*\alpha'})  \quad \text{Eq. 23}$$

In Equation 23, β and α' are fitting parameters, and when required, the observed θ(λ) (or λ(θ)) is fitted by smoothing functions such as Equation 23. In Equation 23, the value for θ* is given by Equation 24 as follows:

$$\theta^* = \frac{\theta}{\theta_0} \quad \text{Eq. 24}$$

In Equation 24, $\theta_0$ is the liquid content at position x=0, for example shown in FIG. 3. One advantage to using equation 23 is that the closed-form relationship for the transport parameter can be obtained (See Equation 25 as follows). Alternatively, in some general cases, a standard computational approach known as "the smoothing spline" can be employed to remove the noise from the data obtained by NMR and/or other means. The smoothing spline is a method of smoothing or fitting a smooth curve to a set of noisy observations using a spline function. For example, detail for using such a function is provided in "The Theory of Splines and Their Applications" by Ahlberg, J. H., Nilson, E. N., and Walsh, J. L. in Mathematics in Science and Engineering, New York: Academic Press, 1967.

At step 210, using either the directly measured λ(θ) data for volumetric liquid content spatial distribution along the shale sample θ(x) from step 206 or using the smoothed data for λ(θ) from step 208, data for λ(θ) is used to estimate the transport parameter D(θ). Equation 20 is used to calculate D(θ) from λ(θ) as follows:

$$D(\theta) = \frac{\int_{\theta_i}^{\theta} \frac{\lambda}{n+1} d\theta}{\left|\frac{d\theta}{d\lambda}\right|^n} \quad \text{Eq. 20}$$

In Equation 20, $\theta_i$ is the initial liquid content of the shale sample before the spontaneous imbibition test is performed at step 202 and n is the value obtained in Step 204. Once the unconventional flow index n and the transport parameter D(θ) have been calculated, at step 212 the flux "q" for the liquid flow of unconventional liquid imbibition into the low-permeability formations can be calculated according to Equation 12 shown previously. Using Equation 14, $$\frac{\partial \theta}{\partial t}$$

can be calculated with the flow index and the transport parameter, which is useful to show the increased liquid content per time caused by imbibition in an unconventional, low-permeability medium, such as a low-permeability, shale-rock-containing hydrocarbon-bearing formation.

Figure 8:
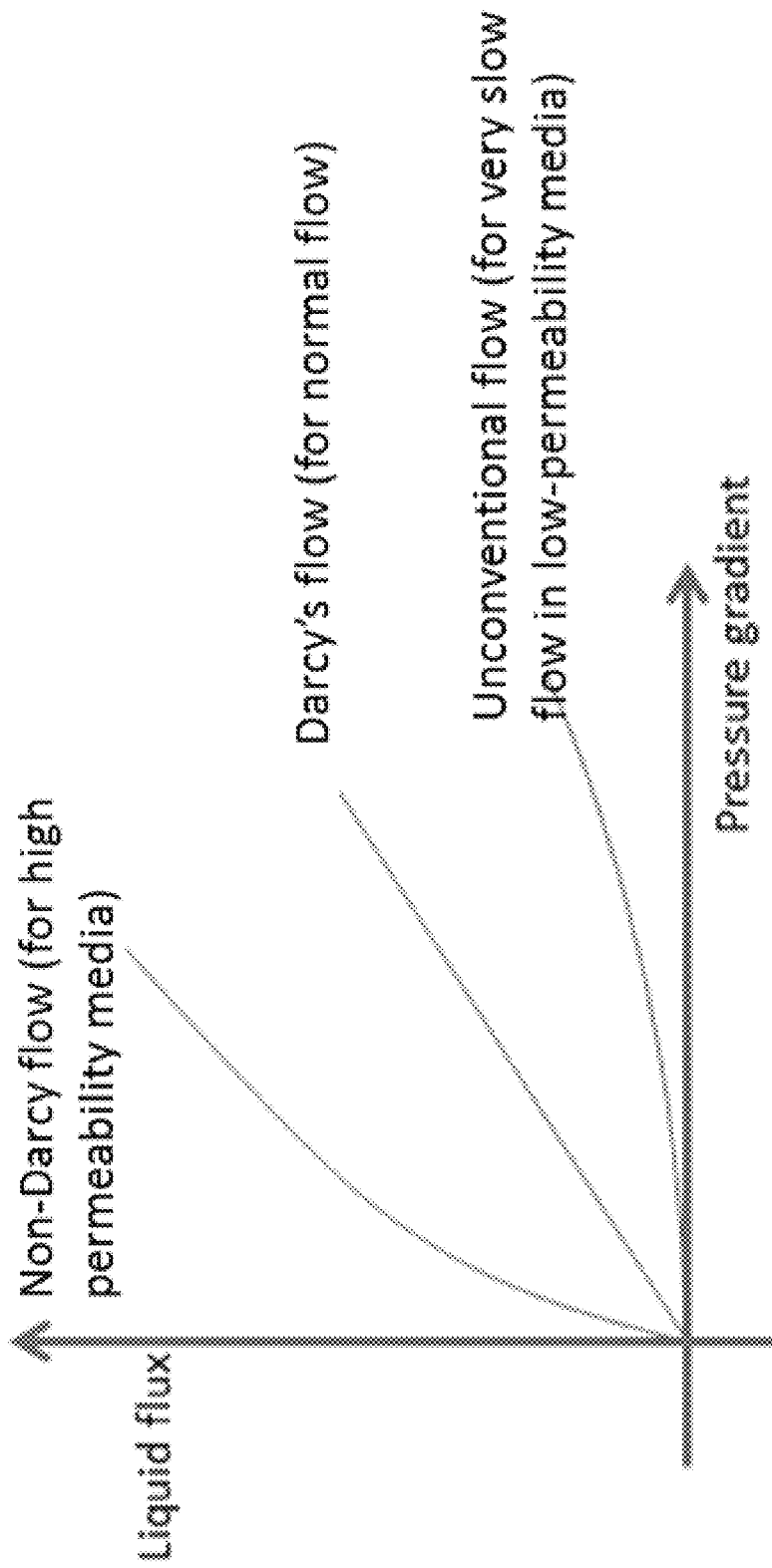
FIG. 8 is a graph showing liquid flux vs. pressure gradient for Darcian, non-Darcian, and unconventional flow regimes.

Referring briefly to FIG. 8, a graph showing Darcian, non-Darcian, and unconventional flow regimes is shown. Typically, the term "non-Darcy" flow refers to high permeability media with fast or turbulent flow. In the present disclosure, as discussed throughout, the methods address determining flow rate for very slow flow in low-permeability media.

Experiments

As noted above, one assumption in the methods of the present disclosure is that liquid flux is a power function of pressure gradient (see, for example, Equation 10). This assumption results, in part, in a relationship between cumulative imbibition into a sample and time, shown by Equation 22. The practical application of this assumption is demonstrated by a comparison between the relationship developed above into Equation 22 and relevant experimental observations. Equation 22 has been compared with data of spontaneous imbibition tests reported by Hu and Ewing (Hu, Q. H., and R. P. Ewing, 2014. Integrated experimental and modeling approaches to studying the fracture-matrix interaction in gas recovery from Barnett shale. Report 09122-12. University of Texas at Arlington) and Roychaudhuri and Jessen, as cited above. The data sets and the associated laboratory test procedures are documented by these authors, and the related test conditions are consistent with those specified in Equation 15 above.

In Hu and Ewing, the test samples were from the Barnett shale formation. The samples were cut into rectangular prisms at about 15 mm and then oven-dried at 60° C. for at least 48 hours before being subject to the imbibition experiments. The sample bottom was submerged to a depth 1 mm in a water reservoir. Care was taken to minimize (or eliminate) evaporation from other surfaces of the samples and allow air escape from the top.

Referring now to FIG. 4, a graph showing observed cumulative imbibition as a function of time for a Barnett shale sample from Hu and Ewing is shown. Cumulative imbibition was monitored by automatically recording the sample weight change over time, as fluid imbibed into the samples. The y-axis of the graph is shown in millimeters ("mm") in log scale which represents a depth into the sample. For example, with the mass of the imbibed fluid known (from being measured with time) and the density of the imbibed fluid known, the volume of the imbibed fluid can be calculated. Then, by dividing by the cross sectional area of the sample prism, the cumulative imbibition can be plotted in units of length (here a depth into the column).

Observations for a typical sample are shown in FIG. 4. At very early times (less than 1 min), imbibition increases abnormally quickly, which may, without being bound by any theory, result from the boundary effects or balance stability problem. However, after that, the relationship between cumulative imbibition and time follows a straight line in the log-log scale with a slope of 0.262. Such an observation is consistent with Equation 22 with n=2.82. Similar results were found (with slopes ranging from 0.214 to 0.357) for all the other samples investigated. This further confirms the existence of unconventional liquid flow behavior in shale. As previously indicated, Darcian flow behavior corresponds to a slope of 0.50.

The observed unconventional flow behavior, for example that shown in FIG. 4, has been attributed to poor pore connectivity in low-permeability media. However, Equations 10 through 22 above mathematically demonstrate that the observed unconventional liquid flow is a direct result of the nonlinearity between imbibition flux and pressure gradient. Without being bound by any specific theory, the nonlinearity may be caused by the strong solid-liquid interaction in low permeability media, rather than pore connectivity.

Referring now to FIG. 5, a graph showing comparisons between the imbibition data of Roychaudhuri et al. (cited herein) and Equation 22, derived herein, is presented. A similar test procedure to that used in Hu and Ewing was used by Roychaudhuri et al. in their spontaneous imbibition tests of shale samples from the Marcellus formation. In the plot of cumulative imbibition versus $t^{1/2}$, the observations could not be represented by a single straight line. Darcy's law could not be used; instead, two separated straight lines were used with two different slopes to represent the data, and the first straight line was interpreted (with a relatively large slope) as a signature of imbibition to micro-fractures.

The data can be adequately represented by Equation 22 as shown in FIG. 4. Sample #11 has a slope of 0.47 in FIG. 5, which is very close to 0.5, indicating that liquid flow is close to Darcian flow in this case. Nevertheless, most shale samples are characterized by unconventional flow and the methods presented herein (discussed in the above section) can be applied to both Darcian and unconventional flow processes.

As indicated in Equation 12, parameters n and $D(\theta)$ need to be given for modeling unconventional liquid flow. Based on the analytical results for one-dimensional spontaneous imbibition process shown in Equations 20 and 22, a laboratory test procedure to estimate n and $D(\theta)$ is proposed herein.

The laboratory test is designed in such a way that test conditions are consistent with initial and boundary conditions to obtain Equations 20 and 22. Imbibition occurs from one end of a shale column (not from its sides) and the length of the column should be long enough such that it can be approximately considered infinite for the imbibition. Considering the length of a test column of shale to be approximately infinite for imbibition should be easily satisfied in practice because imbibition into shale sample is a slow process.

Care also should be taken such that evaporation from the shale column is eliminated or minimized. Afterward, the cumulative imbibition as a function of time, M(t), is monitored. The log-log plot of cumulative imbibition versus time, see, for example FIGS. 4 and 5, allows for determination of the parameter n by fitting the data with Equation 22. The slope in a plot similar to the plots in FIGS. 3 and 4 is equal to 1/(n+1).

In order to estimate $D(\theta)$ from Equation 20, $\theta(\lambda)$ (or $\lambda(\theta)$) need to be experimentally determined. Responsive to the transformation given in Equation 17, $\theta(\lambda)$ can be calculated from volumetric liquid content spatial distribution $\theta$ for a given time, or from $\theta$ as a function of time at a given location, when the parameter n is known. In some embodiments, the use of $\theta$ spatial distribution at the time when imbibition test is finished is considered more practical. Since the imbibition depth is likely small, a high-resolution measurement of $\theta$ distribution along the shale column is required.

In some embodiments, a Nuclear Magnetic Resonance (NMR)-based method is used for such a purpose. NMR signal intensity is proportional to the quantity of the mobile protons in a sample and is an accurate method to measure fluid content in rock core plugs in a laboratory setting. Moreover, NMR is a routine logging tool to measure water and mobile hydrocarbons downhole. When combined with pulsed field gradient, NMR can also measure liquid content in a selected volume or slice of a rock.

For many practical reasons, an observed $\theta$ spatial distribution is often not smooth and involves certain degrees of fluctuation, which may in some embodiments cause some problems with calculating $D(\theta)$ from Eq. 20 when directly observed $\theta(\lambda)$ (or $\lambda(\theta)$) is employed. Since $\theta$ distributions generally follow certain regular shapes, a number of empirical algebraic expressions for $\theta(\lambda)$ exist and can be used to fit observed $\theta(\lambda)$ data adequately (e.g., Brutsaert W., 1982. Some exact solutions for non-linear desorptive diffusion. Journal of Applied Mathematics and Physics 33: 540-546; Evangelides C., Arampatzis G., and Tzimopoulos C., 2010. Estimation of soil moisture profile and diffusivity using simple laboratory procedures. Soil Science 175(3): 118-127). These expressions correspond to smooth curves. Furthermore, these expressions allow for derivation of algebraic expressions for $D(\theta)$ that are convenient to use in modeling studies.

To demonstrate the usefulness of the treatment discussed above, Equation 23 provides an expression for $\lambda(\theta)$ as follows:

$$\lambda = \beta(1 - \theta^{*\alpha'}) \qquad \text{Eq. 23}$$

In Equation 23, the value for $\theta^*$ is given by Equation 24 as follows:

$$\theta^* = \frac{\theta}{\theta_0} \qquad \text{Eq. 24}$$

Figure 6:
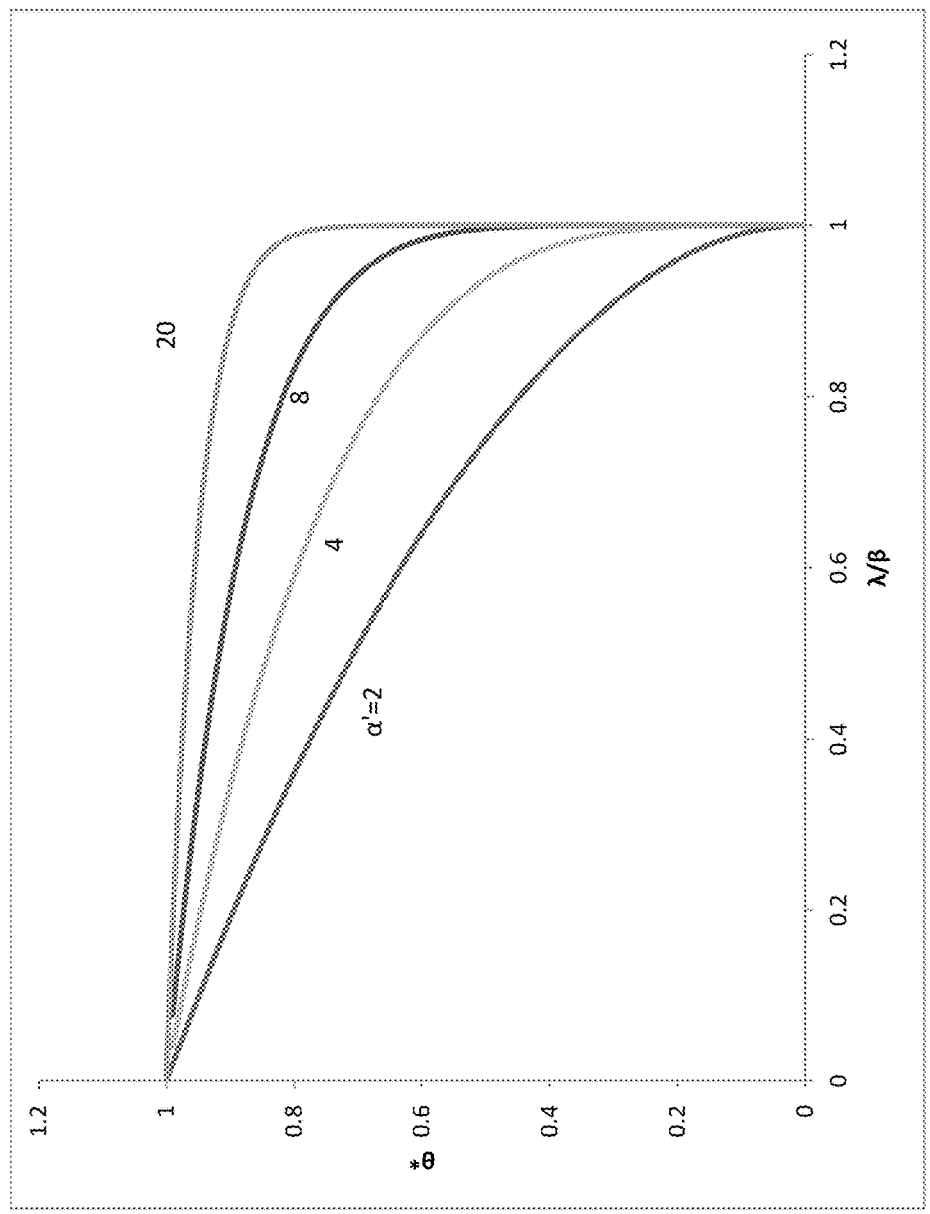
FIG. 6 is a graph showing curves for several α' values, where α' is a fitting parameter used in Equation 23 as follows.

Referring now to FIG. 6, a graph showing curves for several $\alpha'$ values, where $\alpha'$ is a fitting parameter used in Equation 23, is provided. A large $\alpha'$ value corresponds to a relatively sharp liquid content profile and a small $\alpha'$ value to a gradually varying profile. By substituting Equation 23 into Equation 20, this yields Equation 25, shown as follows:

$$D(\theta) = \frac{\beta^{n+1}(\alpha'-1)^n}{\theta_0^{n-1}} \left[ (\theta^* - \theta_i^*) - \frac{(\theta^*)^{\alpha'+1} - (\theta_i^*)^{\alpha'+1}}{\alpha'+1} \right] (\theta^*)^{(\alpha'-1)n} \qquad \text{Eq. 25}$$

The values for parameters $\alpha'$ and $\beta$ can be determined by fitting the $\theta(\lambda)$ data with Equation 23, which is subject to the constraint shown in Equation 26:

$$\int_{\theta_i}^{\theta_0} \lambda d\theta = \beta\theta_0 \left[ (1-\theta_i^*) - \frac{1-(\theta_i^*)^{\alpha'+1}}{1+\alpha'} \right] \quad \text{Eq. 26}$$

In Equation 26, a value for the left hand side of Equation 26 is determined when the cumulative imbibition (M(t)) data is fitted with Equation 22. From the derivation of Equation 22, it becomes apparent that Equation 26 is a constraint associated with liquid mass balance.

Darcy's law is not always adequate for describing liquid flow processes in shale formations, in part because of the strong solid-liquid interaction in low-permeability media. Information recounted herein indicates that the relationship between liquid flux and hydraulic (or pressure) gradient, unlike Darcy's law, is often non-linear (or flow behavior is unconventional) for low-permeability media, such as, for example, clay/shale media.

In embodiments of the present disclosure, a phenomenological model is proposed for measuring and/or modeling unconventional flow behavior in which liquid flux is a power function of pressure gradient, and consequently an analytical solution is developed for a one-dimensional spontaneous imbibition problem that obeys the model. The model is validated by comparisons of theoretical and observed relationships between cumulative imbibition and time. Based on the developed analytical solution, a laboratory test procedure has been proposed to accurately estimate parameters for the phenomenological model from spontaneous imbibition tests.

Nuclear Magnetic Resonance (NMR) Imaging of Spontaneous Imbibition

Figure 9:
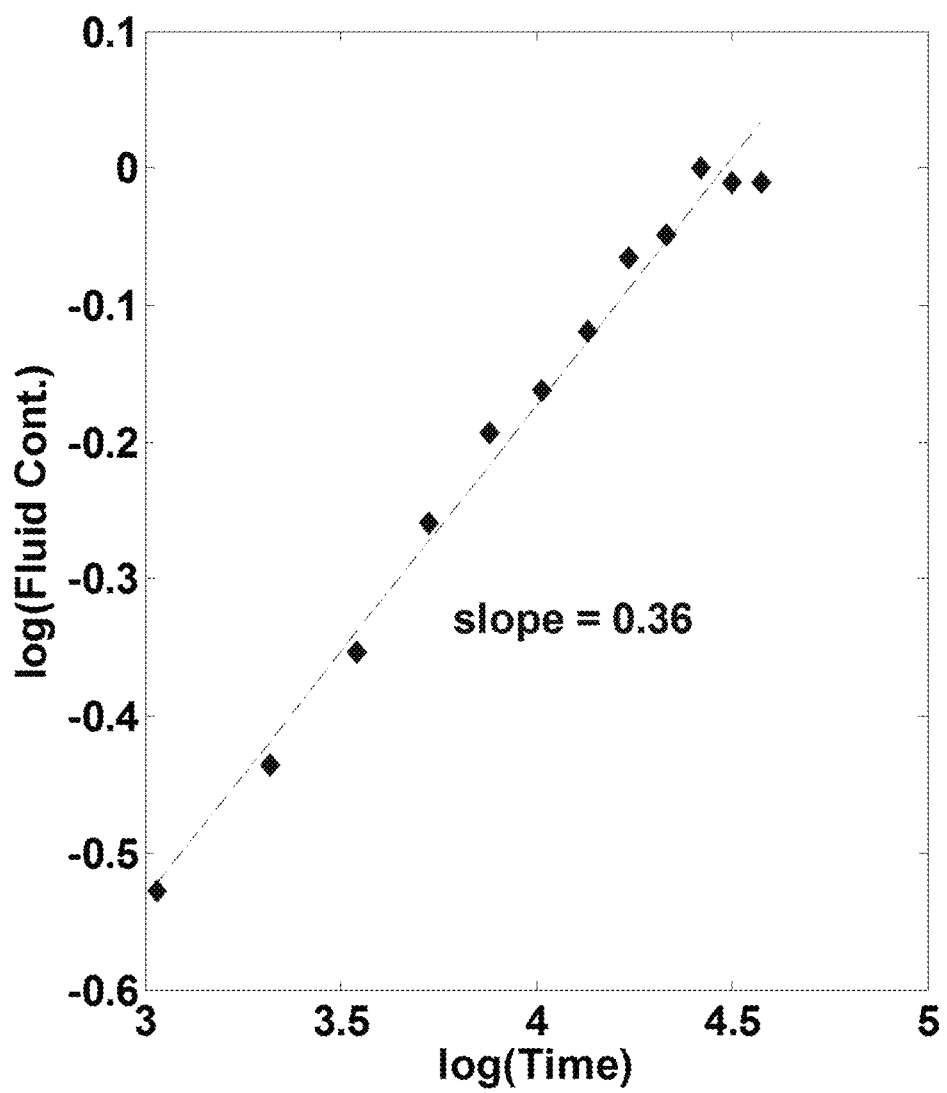
FIG. 9 is a graph showing cumulative imbibed fluid content in a sample with data points for the log of the fluid content of a sample versus the log of time (in minutes) with a fit line of the log-log plot.

Certain imbibition tests with NMR imaging were also conducted by the inventors. Referring now to FIG. 9, when one end of a rock plug (sample) was in contact with water, water was imbibed into it. The content of the cumulative imbibed water was measured using NMR spectroscopy for a Scioto sandstone plug with permeability below 0.1 mD. The integration of each measured fluid profile (along the sample) gives the total fluid content imbibed into the plug at a given time. FIG. 9 shows the linear fitting of the log-log plot of the cumulative imbibed fluid content versus time (in minutes). The slope of the fit line is 0.36, which is less than 0.5. Thus, the flow is unconventional and does not follow Darcy's law.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. These and other similar modifications will readily suggest themselves to those skilled in the art, and are intended to be encompassed within the spirit of the present invention disclosed herein and the scope of the appended claims.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a," "an," and "the" include plural referents, unless the context clearly dictates otherwise.

Optional or optionally means that the subsequently described event or circumstances can or may not occur. The description includes instances where the event or circumstance occurs and instances where it does not occur.

Ranges can be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the disclosure pertains, except when these references contradict the statements made herein.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present invention.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention can suitably comprise, consist or consist essentially of the elements disclosed and can be practiced in the absence of an element not disclosed.

What is claimed is:

1. A method of determining a rate of fluid imbibition into a low-permeability, hydrocarbon-bearing rock matrix, the method comprising the steps of:
    preparing a sample with a length L and a cross-sectional area A obtained from the low-permeability, hydrocarbon-bearing rock matrix for a spontaneous imbibition test with a fluid, the fluid operable for use in hydraulic fracturing of the low-permeability, hydrocarbon-bearing rock matrix;
    conducting the spontaneous imbibition test on the sample, the test including placing an end of the sample into the fluid with an upper portion of the sample exposed to air;
    recording cumulative imbibition of the fluid into the sample over time, the step of recording comprising the use of nuclear magnetic resonance;
    generating a graphical display of a set of data of the log of the cumulative imbibition of the fluid into the sample over time versus a set of data of the log of time;
    determining an unconventional flow index, the unconventional flow index representing unconventional flow, and the unconventional flow index being assimilated by fitting the graphical display to the equation $$V(t) = \left(A \int_{\theta_i}^{\theta_0} \lambda d\theta\right) t^{\frac{1}{n+1}}$$

wherein the power function of the equation (1/(n+1)) is the slope of the line;
  measuring volumetric liquid content spatial distribution along the sample after the spontaneous imbibition test using the area A and a position x along the length L;
  determining a transport parameter of the sample responsive to: the volumetric liquid content spatial distribution along the sample after the spontaneous imbibition test; an initial liquid content of the sample before the spontaneous imbibition test; and the unconventional flow index; and
  determining the rate of fluid imbibition into the low-permeability, hydrocarbon-bearing matrix over time, as a mechanism for liquid uptake by the rock matrix during a well shut-in period, responsive to the unconventional flow index and the transport parameter by calculating liquid content per time by the equation $$\frac{\partial \theta}{\partial t} = -\frac{\partial q}{\partial x} = \frac{\partial}{\partial x}\left(D(\theta)\left|\frac{\partial \theta}{\partial x}\right|^{n-1} \frac{\partial \theta}{\partial x}\right),$$

where θ is liquid content, t is time, q is liquid flux, D(θ) is the transport parameter, and n is the unconventional flow index, to show increased liquid content per time caused by imbibition into the low-permeability, hydrocarbon-bearing rock matrix.

2. The method of claim 1, where the sample is selected from the group consisting of: shale; tight carbonate; and tight sandstone.

3. The method of claim 2, where the sample comprises shale.

4. The method of claim 1, where the step of conducting the spontaneous imbibition test on the sample proceeds for between about 1 minute and about 20 hours.

5. The method of claim 1, where the step of recording cumulative imbibition of the fluid into the sample over time further includes the step of recording the mass of the sample at time intervals during the spontaneous imbibition test to compose recorded sample mass data for recorded time data.

6. The method of claim 1, where the step of measuring volumetric liquid content spatial distribution along the sample after the spontaneous imbibition test is performed by nuclear magnetic resonance.

7. The method of claim 1, where the step of determining a transport parameter of the sample responsive to the volumetric liquid content spatial distribution along the sample after the spontaneous imbibition test further comprises the steps of:
  averaging the spatial distribution of liquid content along the longitudinal direction of the sample over a cross section of the sample by using techniques that provide liquid content measurement with a resolution of 1 mm or less to obtain spatial distribution of liquid content data; and
  smoothing the spatial distribution of liquid content data to remove noisy data.

8. The method of claim 7, where the step of smoothing is performed by a method selected from the group consisting of: utilizing one or more fitting parameters and utilizing a smoothing spline function.

9. The method of claim 1, where the step of recording cumulative imbibition of the fluid into the sample over time includes the step of recording the volume of the liquid content along the sample at time intervals during the spontaneous imbibition test to compose recorded sample volume data for recorded time data.

10. The method of claim 1, where the step of generating a graphical display of a set of data of the log of the cumulative imbibition of the fluid into the sample over time versus a set of data of the log of time includes:
  generating a graphical display of a set of known data; and
  comparing the graphical display of the known data to the graphical display of the set of data of the log of the cumulative imbibition of the fluid into the sample over time versus the set of data of the log of time.

\* \* \* \* \*